(12) United States Patent
Deno (10) Patent No.: US 9,717,429 B2
(45) Date of Patent: Aug. 1, 2017

(54) SYSTEM AND METHOD FOR ANALYZING BIOLOGICAL SIGNALS AND GENERATING ELECTROPHYISOLOGY MAPS

(71) Applicant: St. Jude Medical, Cardiology Division, Inc., St. Paul, MN (US)

(72) Inventor: Don Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 55 days.

(21) Appl. No.: 14/504,163

(22) Filed: Oct. 1, 2014

(65) Prior Publication Data

US 2015/0119738 A1 Apr. 30, 2015

Related U.S. Application Data

(60) Provisional application No. 61/897,863, filed on Oct. 31, 2013.

(51) Int. Cl.
*A61B 5/04* (2006.01)
*A61B 5/0468* (2006.01)
(Continued)

(52) U.S. Cl.
CPC .......... *A61B 5/04012* (2013.01); *A61B 5/021* (2013.01); *A61B 5/042* (2013.01);
(Continued)

(58) Field of Classification Search
CPC ... A61B 5/04012; A61B 5/021; A61B 5/0468; A61B 5/7435
(Continued)

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| CN | 102688031 | 9/2012 |
| CN | 103327887 | 9/2013 |

(Continued)

OTHER PUBLICATIONS

International Search Report and Written Opinion for PCT/US2014/058970 dated Jan. 14, 2015.
(Continued)

*Primary Examiner* — Carl H Layno
*Assistant Examiner* — Jon Eric C Morales
(74) *Attorney, Agent, or Firm* — Wiley Rein LLP (57) ABSTRACT

A method of generating a cardiac electrophysiology map includes receiving a reference biological signal and an electrical signal indicative of electrical activity at a location on a patient's heart. Using a graphical user interface, a practitioner designates at least two trigger point icons, one upward-pointing and one downward-pointing, on a graphical representation of the reference biological signal (e.g., a waveform). By pairing one upward-pointing icon with one downward-pointing icon, a plurality of triggering criteria are defined. Electrophysiology data points are captured and/or added to the electrophysiology map when the triggering criteria are satisfied.

18 Claims, 6 Drawing Sheets

(51) Int. Cl.
*A61B 5/021* (2006.01)
*A61B 5/00* (2006.01)
*A61B 5/042* (2006.01)
A61B 5/0464 (2006.01)

(52) U.S. Cl.
CPC .......... *A61B 5/0468* (2013.01); *A61B 5/7435* (2013.01); *A61B 5/0422* (2013.01); *A61B 5/0464* (2013.01); *A61B 5/743* (2013.01)

(58) Field of Classification Search
USPC ........................................ 600/374, 509, 513
See application file for complete search history.

(56) References Cited

U.S. PATENT DOCUMENTS

| | | | |
|---|---|---|---|
| 6,640,119 | B1 | 10/2003 | Budd et al. |
| 6,728,562 | B1 | 4/2004 | Budd et al. |
| 6,839,588 | B1 | 1/2005 | Rudy |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |
| 2002/0103422 | A1* | 8/2002 | Harder et al. ......... A61B 5/044 600/300 |
| 2007/0276274 | A1 | 11/2007 | Kawada et al. |
| 2008/0009758 | A1 | 1/2008 | Voth |
| 2010/0274123 | A1 | 10/2010 | Voth |
| 2012/0101397 | A1 | 4/2012 | Blomqvist |
| 2012/0184858 | A1 | 7/2012 | Harlev et al. |
| 2013/0245473 | A1 | 9/2013 | Ramanathan et al. |
| 2014/0180721 | A1* | 6/2014 | Cheline ................ G06F 19/321 705/3 |

FOREIGN PATENT DOCUMENTS

| | | |
|---|---|---|
| WO | 2007/137045 | 11/2007 |
| WO | 2007/146864 | 12/2007 |
| WO | 2012/061612 | 5/2012 |

OTHER PUBLICATIONS

International Search Report and Written Opinion for PCT/US2014/058968 dated Jan. 23, 2015.

Gonzalez-Torrecilla et al., Non-Fluoroscopic Electroanatomical Mapping (CARTO System) in the Ablation of Atrial Tachycardias, Revista Espanola De Cardiologia, 2004, 57(1); 37-44.

Raymond W. Sy et al., Modern Electrophysiology Mapping Techniques, Heart, Lung and Circulation, 2012, 21:364-375, Elsevier Inc.

Chugh, Amen et al., "Characteristics of cavotricuspid isthmus-dependent atrial flutter after left atrial ablation of atrial fibrillation", Circulation. pp. 609-615, Feb. 7, 2006.

Hood, Margaret A. et al., "Contribution of myocardium responsible for ventricular tachycardia to abnormalities detected by analysis of signal-averaged ECGs", Circulation, vol. 86, No. 6, pp. 1888-1901, Dec. 1992.

* cited by examiner

«SYSTEM AND METHOD FOR ANALYZING BIOLOGICAL SIGNALS AND GENERATING ELECTROPHYISOLOGY MAPS

CROSS-REFERENCE TO RELATED APPLICATIONS

This application claims the benefit of U.S. provisional application No. 61/897,863, filed 31 Oct. 2013, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for acquisition of signals and generating an electrophysiology map from data collected by an electrophysiology probe (e.g., a contact or non-contact mapping catheter).

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

BRIEF SUMMARY

Disclosed herein is a method of generating a cardiac electrophysiology map, including: acquiring a reference biological signal; establishing a graphical user interface including a graphical representation of the reference biological signal; accepting, through the graphical user interface, a user's designation of a pair of trigger point icons on the graphical representation of the reference biological signal, wherein the pair of trigger point icons define a plurality of triggering criteria, the plurality of triggering criteria including: an upward threshold; a downward threshold; a threshold-crossing time interval; a reference biological signal slope; and a reference biological signal amplitude; acquiring an electrical signal indicative of electrical activity at a location on a patient's heart, wherein the electrical signal is aligned timewise with the reference biological signal; and using the electrical signal to add an electrophysiology data point to the electrophysiology map when the reference biological signal satisfies the plurality of triggering criteria.

The reference biological signal can be a surface electrocardiogram, an intracardiac electrogram (e.g., an endocardial or epicardial electrogram), a blood pressure signal, or any other biological signal that can be pathognomonic for an electrical event of interest (e.g., a particular arrhythmia).

Electrophysiology data points can be added to the electrophysiology map by: analyzing the electrical signal during a time window that encompasses when the reference biological signal satisfies the plurality of triggering criteria; and adding an attribute of interest electrophysiology data point to the electrophysiology data map. The attribute of interest can be a lateness attribute such as a late potential amplitude or time, a peak-to-peak voltage, or any other electrophysiological parameter that may be of interest to a practitioner.

In certain aspects, a refractory period will be defined to prevent the addition of electrophysiology data points from indistinct beats to the electrophysiology map. The refractory period can be defined to start when the reference biological signal satisfies the plurality of triggering criteria, and the next electrophysiology data point can be added to the map only when the reference biological signal next satisfies the plurality of triggering criteria after the refractory period expires.

It is also contemplated that the user can redesignate the reference biological signal and/or the pair of trigger point icons on the graphical representation of the reference biological signal, thereby redefining the plurality of triggering criteria. One or more electrophysiology data points can then be added and/or removed from the electrophysiology map based on the change from the original triggering criteria to the redefined triggering criteria. For example, an electrophysiology data point can be added where the reference biological signal satisfies the redefined triggering criteria, but not the original triggering criteria. Conversely, an electrophysiology data point can be removed where the reference biological signal satisfies the original triggering criteria, but not the redefined triggering criteria.

Also disclosed herein is a method of generating a cardiac electrophysiology map, including: receiving a reference biological signal and an electrical signal indicative of electrical activity at a location on a patient's heart, wherein the reference biological signal and the electrical signal are aligned timewise; establishing a graphical user interface including a graphical representation of the reference biological signal; accepting, through the graphical user interface, a user's designation of at least one upward-pointing trigger point icon and at least one downward-pointing trigger point icon on the graphical representation of the reference biological signal; accepting, through the graphical user interface, a user's designation of a pair of trigger point icons, the pair of trigger point icons including one upward-pointing trigger point icon and one downward-pointing trigger point icon and defining a plurality of triggering criteria; and adding an electrophysiology data point to the electrophysiology map when the reference biological signal satisfies the plurality of triggering criteria.

Based on the designated pair of trigger point icons, the plurality of triggering criteria can include: a reference biological signal slope; a reference biological signal amplitude; and a reference biological signal mean value. In embodiments, the plurality of triggering criteria can also include an upward threshold, defined by the upward-pointing trigger point icon of the pair of trigger point icons; a downward threshold, defined by the downward-pointing trigger point icon of the pair of trigger point icons; and a threshold-crossing time interval, defined by both members of the pair of trigger point icons.

According to certain aspects, a plurality of reference signals and a plurality of pairs of trigger point icons are designated, with each pair of the plurality of pairs including one upward-pointing trigger point icon and one downward-pointing trigger point icon and defining a respective plurality of triggering criteria. Via the graphical user interface, the user can designate various relationships between the respective pluralities of reference biological signals and/or triggering criteria, such as defining Boolean logic relationships (e.g., AND, OR, and NOT in various combinations). Electrophysiology data points can be added to the electrophysiology map only when the reference biological signal(s) satisfy the defined relationship(s) between the respective pluralities of triggering criteria.

In another embodiment, a system for generating a cardiac electrophysiology map includes: a graphical user interface processor configured to: receive, as input, a reference biological signal; establish a graphical user interface including a graphical representation of a reference biological signal; accept a user's designation of a pair of trigger point icons on the graphical representation of the reference biological signal; and define, from positioning of the pair of trigger point icons on the graphical representation of the reference biological signal, a plurality of triggering criteria; and an electrophysiology mapping processor in operable communication with the graphical user interface processor, wherein the electrophysiology mapping processor is configured to: receive, as input, an electrical signal indicative of electrical activity at a location on a patient's heart, wherein the electrical signal is aligned timewise with the reference biological signal; and add an electrophysiology data point to the electrophysiology map using the electrical signal when the reference biological signal satisfies the plurality of triggering criteria.

The plurality of triggering criteria will typically include: a reference biological signal slope; a reference biological signal amplitude; and a reference biological signal mean value. It can also include an upward threshold; a downward threshold; and a threshold-crossing time interval.

It is contemplated that the reference biological signal can be selected from: surface electrocardiograms; epicardial electrograms; endocardial electrograms; blood pressure signals; and any combination thereof.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses and systems for the creation of electrophysiology maps (e.g., electrocardiographic maps). For purposes of illustration, several exemplary embodiments will be described in detail herein in the context of a cardiac electrophysiology procedure. It is contemplated, however, that the methods, apparatuses, and systems described herein can be utilized in other contexts.

Figure 1:
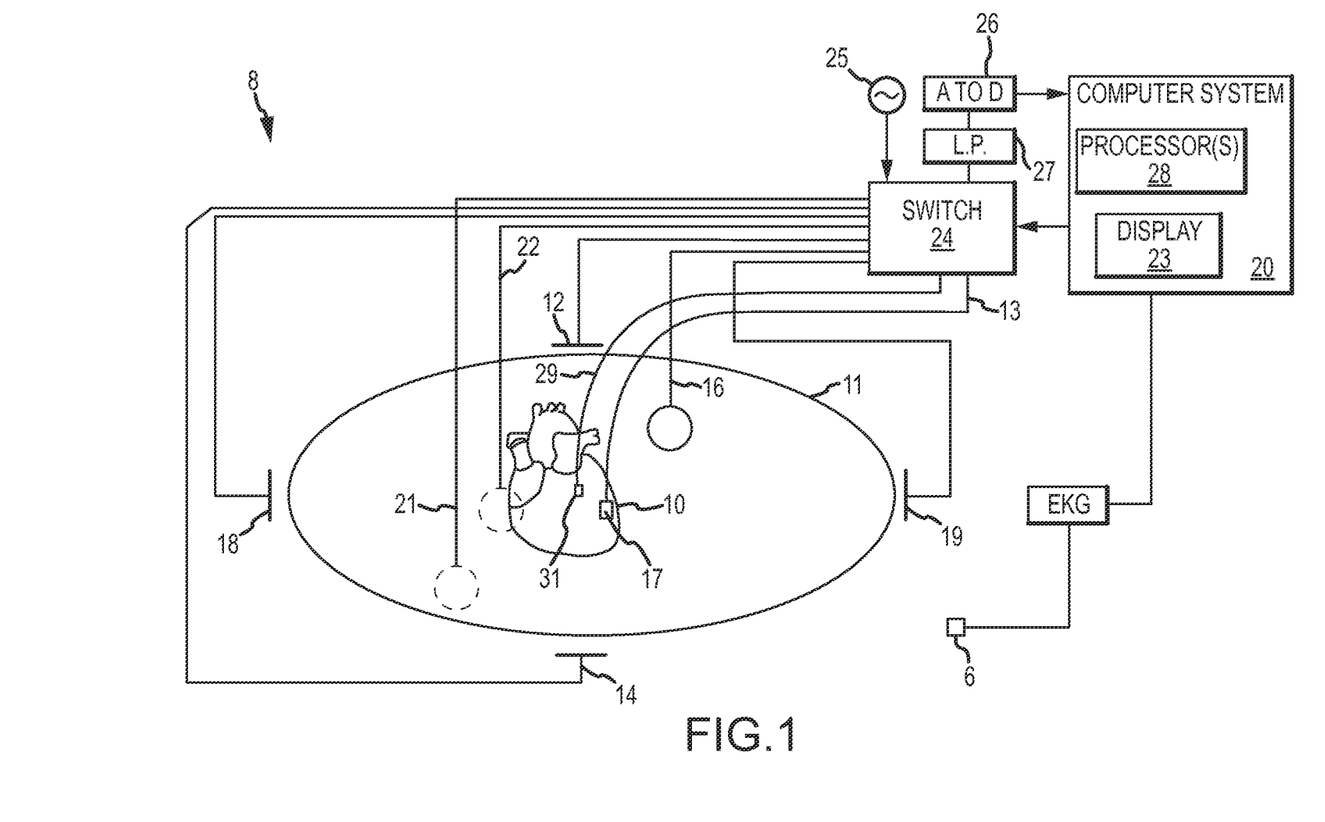
FIG. 1 is a schematic diagram of an electrophysiology system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the measured electrical activity. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, such as, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along the sternum and spine of the patient in the thorax region, and may be referred to as the Chest and Back electrodes. The z-axis electrodes 16, 22 are applied along a third axis generally orthogonal to both the x-axis and the y-axis, such as along the inner thigh and neck regions of the patient, and may be referred to as the Left Leg and Neck electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional surface electrocardiogram ("ECG" or "EKG") system leads in place. In certain embodiments, for example, a standard set of 12 ECG leads may be utilized for sensing electrocardiograms of the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion. This representative catheter electrode 17 can be referred to as a "measurement electrode." Typically, multiple electrodes on catheter 13, or on multiple such catheters, will be used. In one embodiment, for example, system 8 may utilize sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
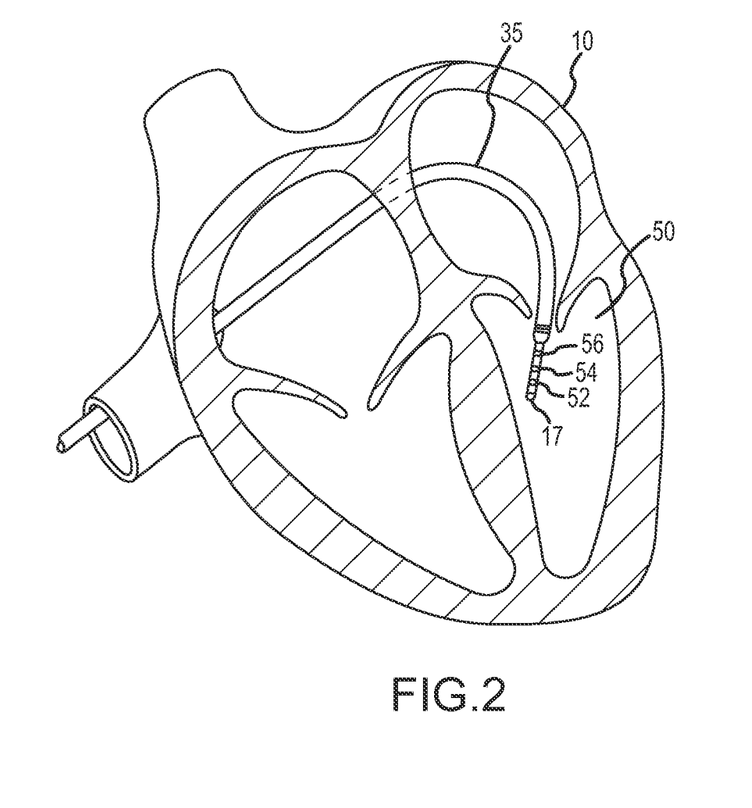
FIG. 2 depicts an exemplary catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the measurement electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The measurement electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the measurement electrodes 17, 52, 54, 56 within heart 10.

The measured voltages may be used by system 8 to determine the location in three-dimensional space of the electrodes inside the heart, such as measurement electrodes 17, 52, 54, 56, relative to a reference location, such as reference electrode 31. That is, the voltages measured at reference electrode 31 may be used to define the origin of a coordinate system, while the voltages measured at measurement electrodes 17, 52, 54, 56 may be used to express the location of measurement electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields.

The localization and mapping systems described in the following patents (all of which are hereby incorporated by reference in their entireties) can also be used: U.S. Pat. Nos. 6,990,370; 6,978,168; 6,947,785; 6,939,309; 6,728,562; 6,640,119; 5,983,126; and 5,697,377.

In general, electrophysiology maps are created from a plurality of electrophysiology data points, each of which includes both measured electrophysiology data (e.g., endocardial and/or epicardial electrograms ("EGMs")) and location data (e.g., information regarding the location of catheter 13 and/or the electrodes thereon), allowing the measured electrophysiology information to be associated with a particular location in space (that is, allowing the measured electrophysiology information to be interpreted as indicative of electrical activity at a point on the patient's heart). For example, U.S. provisional application No. 61/888,719, filed 9 Oct. 2013 ("the '719 application"), which is hereby incorporated by reference in its entirety as though fully set forth herein, describes the creation of lateness maps (e.g., a map that depicts the lateness attributes of the electrical activity at various points on a cardiac surface).

Lateness attributes, which include both late potential ("Late-P") and late activation ("Late-A") attributes, suggest that some myocardial fibers are functional near the measurement electrode, but that they are few in number and therefore low in amplitude and conducting slowly. These conditions are understood to be ripe for the initiation and sustainment of cardiac arrhythmias, such as ventricular tachycardia ("VT"); such tissue also lacks substantial mechanical pump function. Thus, these points are desirable targets for ablation to treat VT.

A Late-P attribute is measured from a common reference point, such as from the peak of a surface ECG R wave, to the end of activity at the site being mapped. A Late-A attribute, on the other hand, is measured from the last large deflection (indicating the end of major local depolarization) to the end of low amplitude activity at that site (indicating the end of nearby depolarizations of small myocardial fibers or pathways, such as might occur in a critical arrhythmia pathway). This is advantageous, as it allows a Late-A attribute to be identified for any electrophysiological signal, whether EGM or ECG, without reference to any overall trigger (e.g., a $V_{PACE}$ event and/or a specific part of a surface QRS or endocardial EGM deflection).

The present disclosure relates to the collection of electrophysiology data points for use in creating electrophysiology maps. The ordinarily skilled artisan will be familiar with various modalities for the acquisition and processing of electrophysiology data points (including, for example, both contact and non-contact electrophysiological mapping), such that extensive discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the maps disclosed herein.

Further, although reference will be made to lateness maps for the sake of explaining the instant disclosure, the present teachings can be applied to the collection of electrophysiology data points for any type (or types) of electrophysiology maps, such as activation time maps or peak-to-peak amplitude maps.

Moreover, it should be understood that an electrophysiology map herein need not be limited to a graphical depiction of a single variable (e.g., lateness) by cardiac location. Indeed, the teachings herein can be used to acquire electrophysiology data points for a broad range of electrophysiology maps, including those that tabulate or otherwise relate multiple electrophysiological characteristics to cardiac locations.

Figure 3:
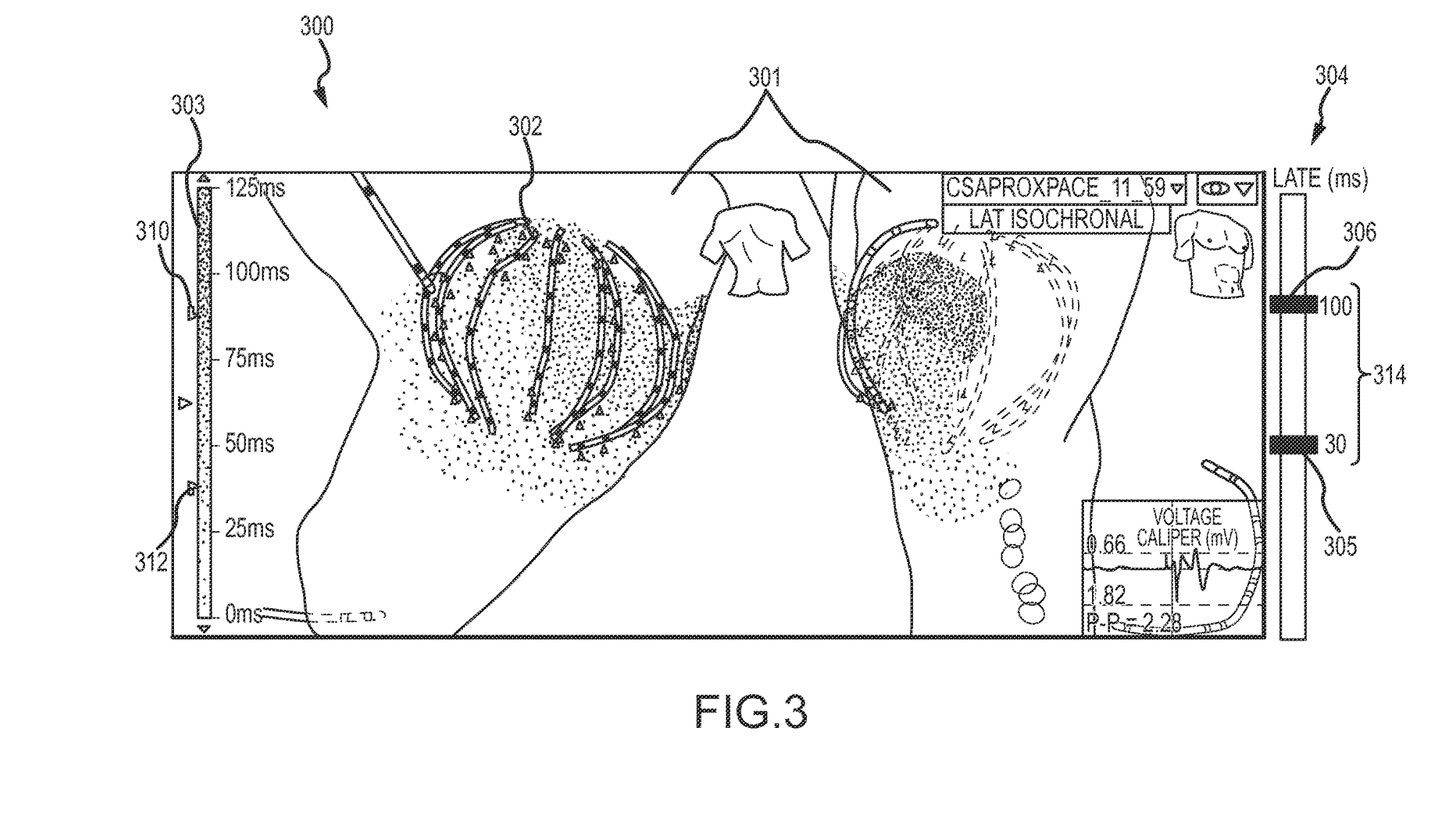
FIG. 3 is a representative lateness map, which is presented as an exemplary electrophysiology map developed according to the teachings herein.

Thus, it is only by way of illustration, and not by way of limitation, that FIG. 3 depicts an exemplary lateness map 300 generated using various aspects disclosed herein and data collected and processed using system 8 (e.g., using computer system 20).

The ordinarily skilled artisan will be familiar with various modalities for the acquisition and processing of electrophysiology data points (including, for example, both contact and non-contact electrophysiological mapping), such that further discussion thereof is not necessary to the understanding of the lateness mapping techniques discussed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the lateness maps discussed herein. Lateness map 300 includes a graphical representation 301 of the portion of the patient's heart that is being mapped, and also depicts a graphical representation 302 of the mapping catheter itself.

An index 303 shows the color- or grey-scale (or other presentation, such as stippling) with which the graphical representation 301 of the heart is generated (e.g., what color or shade of grey corresponds to a particular lateness attribute). Index 303 includes upper bound indicator 310 and lower bound indicator 312. All points with lateness values above upper bound indicator 310 can be presumed to be equally desirable ablation targets. Thus, the presentation scale above upper bound indicator 310 can be undifferentiated (that is, all points with lateness values in excess of upper bound indicator 310 can be presented in the same color, the same level of greyscale, or the like.

Likewise, all points with lateness values below lower bound indicator 312 can be presumed to be equally undesirable ablation targets. Thus, the presentation scale below lower bound indicator 312 can also be undifferentiated.

Between upper and lower bound indicators 310, 312, however, variations in presentation can be used to aid a practitioner in identifying desirable ablation targets.

Also shown in FIG. 3 is a slider bar 304 that can be used to define a lateness threshold and a lateness bound. The lateness threshold T can be user selectable and adjustable, for example using a slider bar 305 as shown schematically in FIG. 3. Likewise, the lateness bound B can be user selectable and adjustable, for example using a slider bar 306 as shown schematically in FIG. 3.

Below the lateness threshold T (e.g., above 30 ms in FIG. 3), one can presume that the "lateness" is part of the original QRS wave rather than a separate "late" feature. Similarly, above the lateness bound B (e.g., above 100 ms in FIG. 3), one can presume that the "lateness" is so far removed from the original QRS wave that it is likely an artifact rather than a separate "late" feature. Together, the lateness threshold T and lateness bound B define a lateness band 314. Points that are suitable targets for ablation and/or other therapies are likely to have lateness attributes falling within this band. The ordinarily skilled artisan will recognize, for example from the disclosure in U.S. application Ser. No. 14/504,174, filed Oct. 1, 2014, which is hereby incorporated by reference as though fully set forth herein, how to select suitable lateness bands 314 for both Late-P and Late-A attribute lateness maps.

Figure 4:
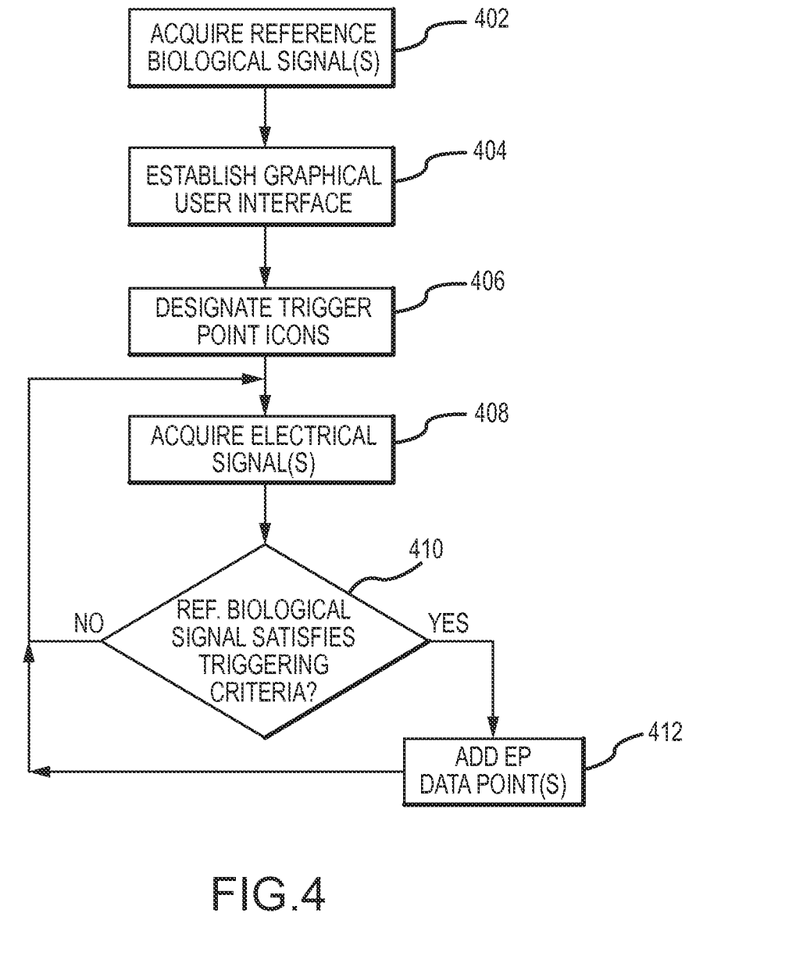
FIG. 4 is a flowchart of representative steps that can be followed to develop an electrophysiology map according to the teachings herein.

FIG. 4 is a flowchart of representative steps that can be carried out to create an electrophysiology map. In some embodiments, the flowchart may represent several exemplary steps that can be carried out by the computer 20 of FIG. 1 (e.g., by one or more processors 28) to generate an electrophysiology map, such as the lateness map depicted in FIG. 3. It should be understood that the representative steps described below can be either hardware- or software-implemented. For the sake of explanation, the term "signal processor" is used herein to describe both hardware- and software-based implementations of the teachings herein.

In block 402, a reference biological signal is acquired. As used herein, the term "reference biological signal" refers to a biological signal that exhibits characteristics of cardiac electrical activity of interest (e.g., a signal that is pathognomonic of a particular arrhythmia of interest), and that is therefore utilized as a reference point to acquire and characterize electrophysiology data for mapping purposes. Suitable biological reference signals include, without limitation, electrocardiogram ("ECG" or "EKG") signals, cardiac electrogram ("EGM") signals, blood pressure (e.g., arterial blood pressure or "ABP") signals, and the like (e.g., pulse plethysmography from oxygen saturation measurements).

Figure 5:
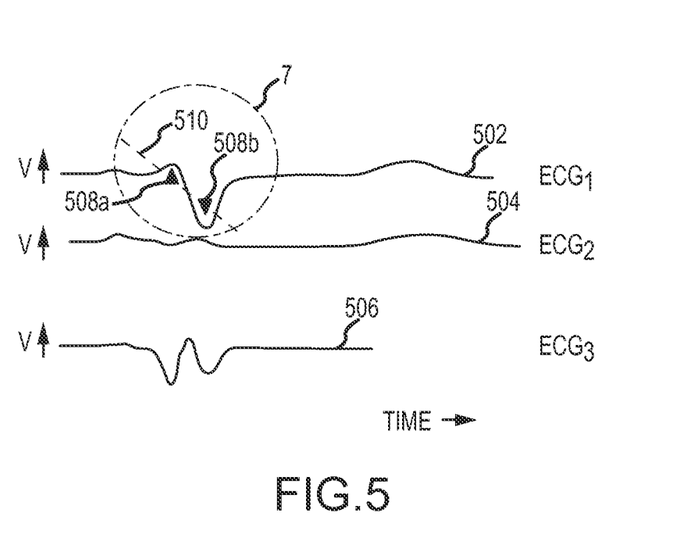
FIG. 5 depicts a representative graphical user interface according to the teachings herein.

In step 404, a graphical user interface ("GUI"), including a graphical representation of the reference biological signal is established. FIG. 5 depicts a representative graphical user interface, including several exemplary ECG signals (e.g., $ECG_1$ 502, $ECG_2$ 504, and $ECG_3$ 506) from which the reference biological signal can be selected.

Of the signals depicted in FIG. 5, $ECG_1$ 502 is the most suitable candidate for use as a reference biological signal. $ECG_2$ 504 is less desirable as a reference biological signal because it is of too low amplitude, while $ECG_3$ 506 is not as suitable as $ECG_1$ 502 because it has two candidate up- and down-slopes. It should be understood that a practitioner will appreciate relative suitability for use as a reference biological signal as between $ECG_1$ 502, $ECG_2$ 504, and $ECG_3$ 506, for example because the ordinarily skilled artisan will recognize that the rS pattern in $ECG_1$ 502 may be pathognomonic for a particular arrhythmia of interest. Indeed, it will often be the case in clinical practice that at least one biological signal (e.g., ECG, EGM, and/or ABP signal) will exhibit characteristics that are pathognomonic for the electrical activity to be mapped.

Using the GUI, the practitioner can designate a pair of trigger points 508a, 508b on the graphical representation of the reference biological signal (e.g., $ECG_1$ 502) in step 406. As shown in FIG. 5, the trigger points 508a, 508b are represented by a pair of triangular icons, one pointing upward (e.g., trigger point 508a) and one pointing downwards (e.g., trigger point 508b).

The pair of trigger points 508a, 508b defines a plurality of triggering criteria, including: an upward threshold, a downward threshold, a threshold-crossing time interval, a reference biological signal slope, and a reference biological signal amplitude. Each of these will be discussed in turn.

The upward threshold is defined by the upward-pointing trigger point icon 508a. The upward threshold is satisfied when the reference biological signal crosses from below to above the upward-pointing trigger point icon 508a. That is, the upward threshold is satisfied when the voltage of $ECG_1$ 502 exceeds the voltage at which upward-pointing trigger point icon 508a is placed.

Conversely, the downward threshold is defined by the downward-pointing trigger point icon 508b. The downward threshold is satisfied when the reference biological signal drops below the downward-pointing trigger point icon 508b. That is, the downward threshold is satisfied when the voltage of $ECG_1$ 502 drops below the voltage at which downward-pointing trigger point icon 508b is placed.

The threshold-crossing time interval is defined as the time between trigger points 508a, 508b. That is, the threshold-crossing time interval defines a necessary separation in time between when the reference biological signal satisfies a first threshold (e.g., the upward threshold) and when it satisfies a second threshold (e.g., the downward threshold).

The reference biological signal slope is defined as the slope of the line 510 connecting the apexes of trigger point icons 508a, 508b. Likewise, the reference biological signal amplitude is defined as the vertical distance between the apexes of trigger point icons 508a, 508b.

Figure 7:
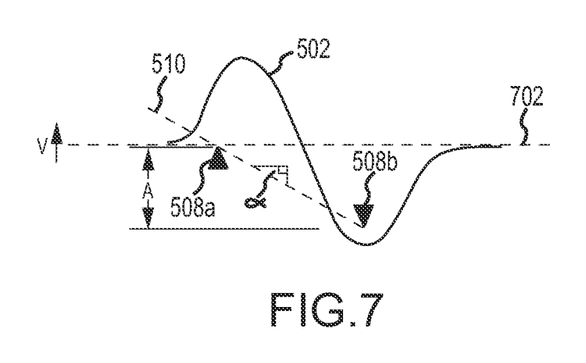
FIG. 7 is a blown-up view of circle 7 in FIG. 5.

FIG. 7 is a detailed view of circle 7 in FIG. 5 that illustrates the placement of trigger point icons 508a and 508b. First, the upward-pointing trigger point icon 508a is placed with respect to isoelectric zero (dashed line 702). Next, the downward-pointing trigger point icon 508b is placed. Downward-pointing trigger point icon 508b has both a level (e.g., a voltage-wise, vertical spacing) and an offset (e.g., a timewise, horizontal spacing) from trigger point icon 508a. Each pair of trigger point icons, therefore, defines three values useful in accordance with the teachings herein: a slope α (which can be positive or negative) of line 510 that connects the apexes of trigger point icons 508a and 508b, a peak-to-peak amplitude A, and a mean value (in the case illustrated in FIGS. 5 and 7, a mean level with respect to isoelectric zero). These three degrees of freedom, in turn, specify a shape or morphologic attribute of the reference biological signal.

The trigger point icons 508a, 508b can also be thought of as defining a box through which a reference biological signal must pass before being added to an electrophysiology map. The direction of trigger point icons 508a, 508b can also be adjusted to require that the signal enter and exit through the sides of the box, therefore limiting it in amplitude, or through the top and bottom of the box, assuring it has at least a minimum or maximum of amplitude.

In step 408, electrical signals indicative of electrical activity at a location on a patient's heart are acquired. The electrical signals can be signals that are continuously acquired (e.g., by electrodes 17, 52, 54, 56 on catheter 13). Continuous signal acquisition is desirable, as it will allow the practitioner to revise the electrophysiology map by redefining trigger points 508a, 508b after the fact. It is contemplated, however, that, in certain aspects, electrical signals are only acquired when the plurality of triggering criteria described above are satisfied.

Figure 6:
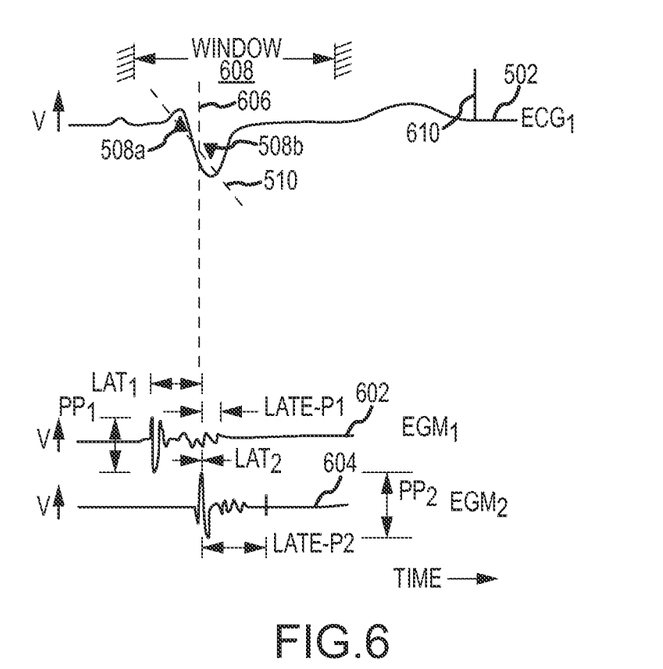
FIG. 6 illustrates several potential reference biological signals juxtaposed with two electrical signals indicative of electrical activity at respective locations on a patient's heart.

FIG. 6 depicts the reference biological signal $ECG_1$ 502 of FIG. 5 juxtaposed with two representative EGM signals, $EGM_1$ 602 and $EGM_2$ 604, each of which is indicative of electrical activity at a respective location on the patient's heart. As shown in FIG. 6, the reference biological signal $ECG_1$ 502 and acquired EGM signals $EGM_1$ 602 and $EGM_2$ 604 are aligned timewise. A timewise reference line 606 is also shown passing through trigger point icon 508b (that is, the point at which it can be determined that the reference biological signal $ECG_1$ 502 satisfies the plurality of triggering criteria).

In decision block 410, it is determined whether the reference biological signal $ECG_1$ 502 satisfies the plurality of triggering criteria. If so, one or more electrophysiology data points corresponding to one or more electrode locations can be added to the electrophysiology map in block 412. As described above, in certain embodiments, decision block 410 can be moved ahead of block 408, such that the electrical signals (e.g., $EGM_1$ 602 and $EGM_2$ 604) are acquired in the first instance only when the reference biological signal $ECG_1$ 502 satisfies the plurality of triggering criteria.

To add an electrophysiology data point to the electrophysiology map, the electrical signal (e.g., $EGM_1$ 602 or $EGM_2$ 604) will typically be analyzed for an attribute of interest during a time window that encompasses when the reference biological signal (e.g., $ECG_1$ 502) satisfies the plurality of triggering criteria. This time window, designated 608 in FIG. 6, is defined relative to timewise reference line 606, and the width and/or start point thereof can be user defined.

Suitable widths of time window 608 are from 20 ms to 200 ms. Further, the start point for time window 608 can be anywhere from 0 ms to 200 ms before or after timewise reference line 606 (e.g., time window 608 need not be symmetrical about timewise reference line 606).

Attributes of interest include, without limitation, lateness attributes (e.g., late potential or "Late-P" attributes; late activation or "Late-A" attributes), peak-to-peak voltages ("PP"), local activation times ("LAT"), peak-negative voltages, fractionation indices, and the like. To aid in understanding these various attributes of interest, $EGM_1$ 602 and $EGM_2$ 604 are annotated with their respective LATs, PPs, and Late-Ps. The ordinarily skilled artisan will understand how to compute LATs and PPs for a given EGM; Late-P attributes (and Late-A attributes), as well as electrophysiology maps of the same, are further described in the '719 application.

To acquire additional electrophysiology data points, a refractory period can be defined that starts when time window 608 begins (or, in some embodiments, when time window 608 closes) and that expires some time later (e.g., at time point 610). Indeed, an additional triggering criteria can be defined to require that the remaining triggering criteria described above (e.g., upward and downward thresholds, threshold-crossing time interval, and reference biological signal slope and amplitude) must be satisfied after expiration of the refractory period. The definition of a refractory period allows for the electrical signals (e.g., $EGM_1$ 602 and $EGM_2$ 604) to be collected and analyzed during time window 608 without inadvertently defining a new, overlapping time window if the remaining triggering criteria are satisfied a second time within the refractory period. A suitable refractory period is between 50 ms and 500 ms from the close of time window 608. The ordinarily skilled artisan will appreciate, however, that the refractory period can be defined from any point, not just the opening of time window 608. These additional electrophysiology data points can then be added to (and later removed from) the electrophysiology map, as desired.

Although several embodiments of this invention have been described above with a certain degree of particularity, those skilled in the art could make numerous alterations to the disclosed embodiments without departing from the spirit or scope of this invention.

For example, although the teachings herein are described above in the context of a pair of triggering criteria defined with respect to a single reference biological signal, it is contemplated that multiple reference biological signals, each with respective pairs of trigger points, can be employed in the creation of a single electrophysiology map. The user can also designate various relationships between the respective reference biological signals and/or trigger points, for example using Boolean logic relationships. The ordinarily skilled artisan will understand how to extend the teachings above (e.g., the description of placing a single pair of trigger point icons on a single reference biological signal) to such contexts.

The ordinarily skilled artisan will also appreciate that the teachings herein can be extended through the placement of additional trigger point icons (e.g., three or more triangles) on a single reference biological signal. Each pair of trigger point icons will define a slope, a peak-to-peak amplitude, and a mean level relative to isoelectric zero.

Any combination of trigger point icon pairings (e.g., single pairs on each of several reference biological signals; multiple pairs on a single biological signal) can be combined using Boolean logic, or any other expression of interrelationship, to determine when to acquire electrical signals and/or add electrophysiology data points to the electrophysiology map. Likewise, multiple reference biological signals and/or multiple pairs of trigger point icons can be used to capture electrophysiology data points for a plurality of electrical events of interest (e.g., various arrhythmias of interest).

Moreover, the trigger point icons can be manipulated to redefine the triggering criteria. As the trigger point icons are manipulated, the electrical signals can be re-analyzed, and electrophysiology data points can be added and/or removed from the electrophysiology map as appropriate. In this manner, a practitioner can experiment with various trigger point icon placements and select the best position(s) for a particular electrophysiology study, a particular arrhythmia, or any other desired aspect.

As still another example, the teachings herein could also be used in pulmonary function studies. In such studies, suitable reference biological signals include, without limitation, airway pressure, flow, and $CO_2$ concentration.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a cardiac electrophysiology map, comprising:
   acquiring a reference biological signal;
   establishing a graphical user interface including a graphical representation of the reference biological signal;
   accepting, through the graphical user interface, a user's designation of a pair of trigger point icons on the graphical representation of the reference biological signal, wherein the pair of trigger point icons define a plurality of triggering criteria, the plurality of triggering criteria comprising:

an upward threshold;
a downward threshold;
a threshold-crossing time interval;
a reference biological signal slope; and
a reference biological signal amplitude;
acquiring an electrical signal indicative of electrical activity at a location on a patient's heart, wherein the electrical signal is aligned timewise with the reference biological signal; and
using the electrical signal to add an electrophysiology data point to the electrophysiology map when the reference biological signal satisfies the plurality of triggering criteria.

2. The method according to claim 1, wherein the reference biological signal comprises a surface electrocardiogram.

3. The method according to claim 1, wherein the reference biological signal comprises an intracardiac electrogram.

4. The method according to claim 1, wherein the reference biological signal comprises a blood pressure signal.

5. The method according to claim 1, wherein using the electrical signal to add an electrophysiology data point to the electrophysiology map comprises:
analyzing the electrical signal during a time window that encompasses when the reference biological signal satisfies the plurality of triggering criteria; and
adding an attribute of interest electrophysiology data point to the electrophysiology data map.

6. The method according to claim 5, wherein the attribute of interest comprises a lateness attribute.

7. The method according to claim 6, wherein the lateness attribute comprises a late potential ("Late-P") attribute.

8. The method according to claim 6, wherein the lateness attribute comprises a late activation ("Late-A") attribute.

9. The method according to claim 5, wherein the attribute of interest comprises a voltage.

10. The method according to claim 1, further comprising:
defining a refractory period that starts when the reference biological signal satisfies the plurality of triggering criteria; and
repeating the step of using the electrical signal to add an electrophysiology data point to the electrophysiology map when the reference biological signal satisfies the plurality of triggering criteria after expiration of the refractory period.

11. The method according to claim 1, further comprising:
accepting, through the graphical user interface, a user's redesignation of the pair of trigger point icons on the graphical representation of the reference biological signal, the redesignated pair of trigger point icons redefining the plurality of triggering criteria; and
using the electrical signal to:
add at least one electrophysiology data point to the electrophysiology map, the at least one electrophysiology data point added to the electrophysiology map corresponding to a time when the reference biological signal satisfied the redefined plurality of triggering criteria, but not the original triggering criteria; or
remove at least one electrophysiology data point from the electrophysiology map, the at least one electrophysiology data point removed from the electrophysiology map corresponding to a time when the reference biological signal satisfied the original triggering criteria, but not the redefined triggering criteria.

12. A method of generating a cardiac electrophysiology map, comprising:
receiving a reference biological signal and an electrical signal indicative of electrical activity at a location on a patient's heart, wherein the reference biological signal and the electrical signal are aligned timewise;
establishing a graphical user interface including a graphical representation of the reference biological signal;
accepting, through the graphical user interface, a user's designation of at least one upward-pointing trigger point icon and at least one downward-pointing trigger point icon on the graphical representation of the reference biological signal;
accepting, through the graphical user interface, a user's designation of a pair of trigger point icons defining a plurality of triggering criteria, the pair of trigger point icons including one upward-pointing trigger point icon of the designated at least one upward-pointing trigger point icon and one downward-pointing trigger point icon of the designated at least one downward-pointing trigger point icon; and
adding an electrophysiology data point to the electrophysiology map when the reference biological signal satisfies the plurality of triggering criteria,
wherein the plurality of triggering criteria comprises:
a reference biological signal slope;
a reference biological signal amplitude; and
a reference biological signal mean value.

13. The method according to claim 12, wherein the plurality of triggering criteria further comprises:
an upward threshold, defined by the upward-pointing trigger point icon of the pair of trigger point icons;
a downward threshold, defined by the downward-pointing trigger point icon of the pair of trigger point icons; and
a threshold-crossing time interval, defined by both members of the pair of trigger point icons.

14. The method according to claim 12, wherein:
a plurality of pairs of trigger point icons are designated, each pair of the plurality of pairs defining a respective plurality of triggering criteria and including one upward-pointing trigger point icon of the designated at least one upward-pointing trigger point icon and one downward-pointing trigger point icon of the designated at least one downward-pointing trigger point icon;
the graphical user interface accepts a user's designation of a relationship between the respective pluralities of triggering criteria; and
an electrophysiology data point is added to the electrophysiology map only when the reference biological signal satisfies the relationship between the respective pluralities of triggering criteria.

15. The method according to claim 14, wherein the relationship between the respective pluralities of triggering criteria is expressed in Boolean logic.

16. A system for generating a cardiac electrophysiology map, comprising:
a graphical user interface processor configured to:
receive, as input, a reference biological signal;
establish a graphical user interface including a graphical representation of a reference biological signal;
accept a user's designation of a pair of trigger point icons on the graphical representation of the reference biological signal; and
define, from positioning of the pair of trigger point icons on the graphical representation of the reference biological signal, a plurality of triggering criteria; and an electrophysiology mapping processor in operable communication with the graphical user interface processor, wherein the electrophysiology mapping processor is configured to:
  receive, as input, an electrical signal indicative of electrical activity at a location on a patient's heart, wherein the electrical signal is aligned timewise with the reference biological signal; and
  add an electrophysiology data point to the electrophysiology map using the electrical signal when the reference biological signal satisfies the plurality of triggering criteria,
wherein the plurality of triggering criteria comprises:
  a reference biological signal slope;
  a reference biological signal amplitude; and
  a reference biological signal mean value.

17. The system according to claim 16, wherein the plurality of triggering criteria further comprises:
  an upward threshold;
  a downward threshold; and
  a threshold-crossing time interval.

18. The system according to claim 16, wherein the reference biological signal is selected from one or more of a surface electrocardiogram, an epicardial electrogram, an endocardial electrograms, and a blood pressure signal.

* * * * *